Jan. 24, 1961 E. W. LOWDEN Plant Pat. 2,013
RASPBERRY PLANT
Filed March 24, 1960
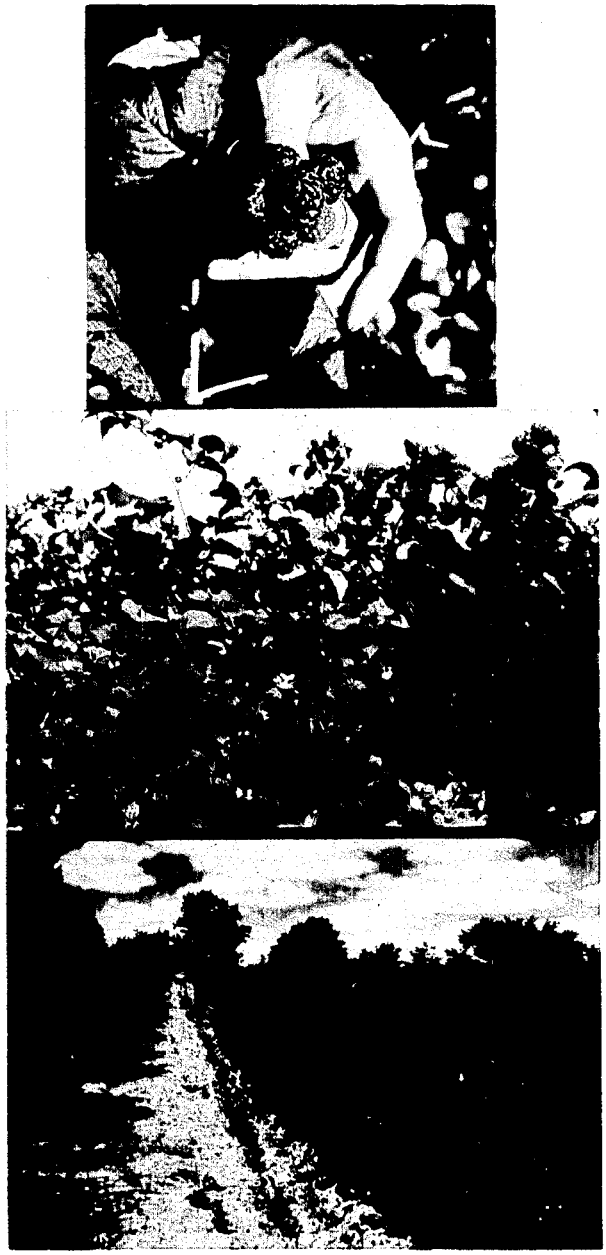
INVENTOR
Edward W. Lowden
BY Robb & Robb
ATTORNEYS United States Patent Office Plant Pat. 2,013
Patented Jan. 24, 1961

2,013

RASPBERRY PLANT

Edward W. Lowden, Ancaster, Ontario, Canada

Filed Mar. 24, 1960, Ser. No. 17,444

1 Claim. (Cl. 47—62)

The present invention relates to a new and distinct variety of black raspberry plant which was originated by me as a cultivated seedling which I derived from a special breeding program conducted by me on my property at Ancaster, Ontario, Canada.

For many years, I had been and still am engaged in the commercial growing of vegetables and berries. In the course of these operations, I became interested in experimental breeding work which I undertook in an effort to obtain new and improved vegetable and berry varieties. As a part of this work, I made crosses of various black and purple raspberry varieties, among others, but because of a prolonged illness, my breeding records were not kept in detail or in a complete form and I am therefore unable to identify with absolute certainty the particular parents of the new seedling referred to above, although I believe that it resulted from a cross of "Bristol Black" (unpatented) and "Sodus Purple" (unpatented), which are two of the many varieties which I used and crossed in my breeding work.

As the result of this breeding, and regardless of the uncertain parentage of my new black raspberry, I have achieved an improved variety which I believe is definitely different from any other variety heretofore known, and which is endowed with important and commercially valuable features which constitute a unique combination in the class of black raspberries, as evidenced by the following characteristics which are outstanding in my new variety:

(1) Vigorous and upright canes;

(2) A distinctive cane color ranging between Dark Red and Bright Maroon which is particularly outstanding in the dormant stage, and the total or almost complete absence of gray bloom on the canes, contrary to most black and purple raspberries;

(3) A habit of bearing the fruit in large drupelets;

(4) An exceptionally large individual berry size;

(5) Juicy quality of the berries and their distinctive flavor which is characterized by a delectable blend of both black and red raspberry flavor, with the black flavor predominating;

(6) Exceptionally small fruit seeds (smaller than those of any black or purple raspberries heretofore known to me, and smaller than most reds);

(7) A relatively late ripening habit;

(8) Superior canning qualities surpassing all other blacks or purples heretofore known to me; and (9) Exceptionally good resistance to drought.

Asexual reproduction of my new variety by "tipping" or "tip-layering" (a method of vegetative propagation which involves covering the tips of the canes with soil so that they will take root), as performed by me on my cultivated property at Ancaster, Ontario, Canada, shows that the foregoing characteristics and distinctions come true to form and are established and transmitted through succeeding propagations.

The accompanying drawing shows typical specimen plants of my new black raspberry variety as grown in a cultivated outdoor row, as well as typical foliage and berries shown on a somewhat larger scale in different stages of development, and also a typical drupelet of berries in different stages of maturity as shown on a still further enlarged scale, all as depicted in color as nearly true as it is reasonably possible to attain in a composite color illustration of this character.

The following is a detailed description of my new variety, as based upon observations made at Ancaster, Ontario, Canada, and with color terminology in accordance with the Nickerson Color Fan, published by Munsell Color Company of Baltimore, Maryland, except where Munsell Color Chart is indicated or where general color terms of ordinary dictionary significance are obvious:

Parentage: A seedling of unknown parentage but believed to have resulted from a cross of "Bristol Black" and "Sodus Purple."

Propagation: Holds its distinguishing characteristics through succeeding propagations by tip-layering; throws occasional sucker plants from the roots.

Dates of first and last picking: About July 17 and about August 7 respectively, but usually ¾ of the fruit crop can be picked within a period of about one week ranging about July 24 to about July 31.

Plant:

*Growth.*—Quite vigorous.

*Root.*—Vigorous.

*Crown.*—Branched; averages from 3 to 5 canes.

*Leaves.*—Many; from medium to large size.

*Canes.*—Size—medium. Color—between Strong Red, color 5R 4/12 and Dark Red, color 5R 3/7; with little or no grayish overcast. Thorns—average about ⅛ inch long; extend at right angles to canes.

Bloom: Medium late. Size—medium.

Fruiting stems: Long; stout; upright.

Fruit: Borne in large drupelets; individual berries are exceptionally large in size.

*Color.*—Dull purplish black when ripe, but more like a purple until fully ripe; near color 2.5RP 3/2 (Munsell); may be generally described as purplish red before fully ripe, which changes to dark steel gray when fully ripe because of overcast of light gray bloom on fruit, which tends to smother the purplish red color and give it a more neutral dark steel gray color value between 4.0 and 4.5 (Munsell); color not quite as dark as some black raspberries, but definitely darker when fully ripe than most purple raspberries, and definitely black in appearance—not purple.

*Flesh.*—Juicy.

*Flavor.*—Sweet; rich; blend of black and red raspberry flavor, with black the flavor predominating.

*Seeds.*—Very small.

Soil where grown: Well-drained sandy loam, but will also thrive in silt or light clay loam.

Culture: Average cultivation; no spraying needed.

Drought resistance: Exceptionally good resistance to drought.

Use: Market; local; dessert; especially superior for canning.

I claim:

A new and distinct variety of black raspberry plant, substantially as herein shown and described, characterized particularly as to novelty by the unique combination of its vigorous and upright canes, a distinctive cane color ranging from Dark Red to Bright Maroon in general color tonality which is particularly outstanding in the dormant stage, attended by a total or almost complete absence of gray bloom on the canes, a habit of bearing the fruit in large drupelets, with the individual berries being purplish red in color until fully ripe and the color changes to dull purplish black overcast with a steel gray bloom, large size, juicy quality and distinctive flavor of the berries, said flavor being characterized by a delectable blend of both black and red raspberry flavor, with the black flavor predominating, exceptionally small fruit seeds, a relatively late ripening habit, superior canning qualities, and exceptionally good resistance to drought.

No references cited.